United States Patent [19]
Dyckman et al.

[11] Patent Number: 5,962,751
[45] Date of Patent: Oct. 5, 1999

[54] PHENOL TAR DESALTING METHOD

[75] Inventors: Arkady S. Dyckman; Yelena N. Sarge; Vladimir I. Sarge; Boris I. Gorovits, all of St. Petersburg; Yury I. Petrov, Novokuibishevsk; Leontii M. Krasnov, Novokuibishevsk; Alexander S. Malinovskii, Novokuibishevsk; Sergey N. Chernukhin, Novokuibishevsk; Anatoly D. Sorokin, Novokuibishevsk, all of Russian Federation; John V. Fulmer, Mt. Vernon, Ind.

[73] Assignee: General Electric Company, Schenectady, N.Y.

[21] Appl. No.: 08/638,416

[22] Filed: Apr. 26, 1996

[51] Int. Cl.⁶ .................................................. C07C 37/24
[52] U.S. Cl. ............................................... 568/757
[58] Field of Search ............................... 568/757

[56] References Cited

U.S. PATENT DOCUMENTS

| | | |
|---|---|---|
| 2,113,951 | 4/1938 | Shuman . |
| 2,301,709 | 11/1942 | Rumscheldt et al. . |
| 4,016,213 | 4/1977 | Yeh et al. . |
| 4,154,964 | 5/1979 | Balg . |
| 4,173,587 | 11/1979 | Wu et al. . |
| 4,207,264 | 6/1980 | Anderson et al. . |
| 4,310,712 | 1/1982 | Langley . |
| 4,358,618 | 11/1982 | Sifniades et al. . |
| 4,929,786 | 5/1990 | Himmele et al. . |
| 5,015,786 | 5/1991 | Araki et al. . |
| 5,017,729 | 5/1991 | Fukuhara et al. . |
| 5,144,094 | 9/1992 | Richmond et al. . |
| 5,254,751 | 10/1993 | Zakoshansky . |
| 5,283,376 | 2/1994 | Dyckman et al. . |
| 5,371,305 | 12/1994 | Hood . |
| 5,672,774 | 9/1997 | Dyckman et al. . |

FOREIGN PATENT DOCUMENTS

| | | |
|---|---|---|
| 57-80332 | 11/1980 | Japan . |
| J5 7080-332 | 11/1980 | Japan . |
| 614084 | 6/1978 | Russian Federation . |
| N940401 | 11/1994 | Russian Federation . |
| 2083546 | 12/1995 | Russian Federation . |

OTHER PUBLICATIONS

Ind. Eng. Chem. Res. 1988, 27, 4–7 "Side Reactions in the Phenol/Acetone Process. A Kinetic Study".

"Side Reactions in the Phenol/Acetone Process. A Kinetic Study" by Pier Luigi Beltrame, Paolo Carniti, Aldo Gamba, Oscar Cappellazzo, Loreno Lorenzoni, & Giuseppe Messina, Ind. Eng. Chem. Res. 1988, 27, 4–7.

Single–stage hydrogenation of the by products of phenol and acetone production [from cumene] A.B. Vol–Epshtein, M.N. Zaharova, & D. Berents. Neftepererabotka I Neftekhim Nauchn.–ekhn. Sb. 1965 (10) 37–9(Russ).

*Primary Examiner*—Gary Geist

[57] ABSTRACT

A tar desalting process wherein the tar containing salts is mixed with dilute aqueous orthophosphoric acid in either a batch or continuous process, allowed to settle into two phases, an organic phase and an aqueous phase containing most of the salts which is then removed from the organic phase. The process removes a high percentage of the salts from the tar and reduces fouling and corrosion of downstream equipment.

13 Claims, No Drawings

PHENOL TAR DESALTING METHOD

This invention relates generally to a process for the manufacture of phenol from cumene and, in particular, relates to a method for recovery of valuable products from the tar byproducts of the process.

In the production of phenol and acetone by oxidation of isopropylbenzene (cumene), the most serious disadvantage is formation of tar by the process. Tar formation can be as high as 10–20 weight percent of the phenol produced. The composition of the tar is typically a complex mixture containing, in weight percent, about:

| | |
|---|---|
| 4–15% | phenol |
| 20–25% | cumylphenols (CP) |
| 20–35% | alpha-methylstyrene dimers (AMS dimers) |
| 3–10% | acetophenone (SP) and dimethylbenzylalcohol (DMBA) |
| 0.2% | water |
| 0.1–3% | inorganic salts and unidentified high molecular weight compounds |
| 100% | Total |

Considering the world-wide production level of phenol, the processing and disposal of byproduct tar from phenol production is a major economic and environmental challenge for phenol producers. As improvements of the phenol process are put into practice, the recovery of valuable products from tar is becoming increasingly difficult The presence of the inorganic salts in the tar increases the complexity of the removal method. These salts include sulfates and phenates of sodium and iron as well as sodium salts of organic acids formed during the oxidation of isopropylbenzene, the acid catalyzed cleavage of cumene hydroperoxide and the subsequent neutralization of the acidic byproducts.

The pH of phenol tar ranges from slightly acid to strongly alkaline, i.e., from 6.5 to 11.

The viscosity of the tar, depending on process operation and operating rates will range from as low as 60 centipoise (cp)to over 2300 centipoise.

The inorganic salts, e.g., sodium sulfate, in the tar raise havoc with the processing equipment employed in recovering the valuable components of the tar. The salts crystallize and cause pipes, heat exchangers and column reboilers to clog. In addition, prevention of equipment corrosion from salt decomposition limits the selection of materials for construction of equipment to corrosion resistant alloys and lined vessels particularly in high temperature operations.

Also the salts can poison hydrogenation and other catalysts used in the recovery process.

Preliminary desalting of the tar before thermal destruction is necessary to reduce reactor corrosion and increase reactor life.

As a result of these problems, there has been very little recovery of useful components from tar and phenol tar has been mostly burned as fuel oil. Even when burning as fuel or incineration for disposal, the presence of salts causes equipment corrosion, air pollution from particulate matter and loss of burner efficiency from encrustation.

One widely used method for salt removal known to the skilled artisan is the use of a dilute sulfuric acid wash of the tar. The wash process is carried out in two steps. In the first, the tar is acidified with dilute sulfuric acid and, in the second, it is washed with water to remove the acid salts and soluble decomposition products.

Another method processes the tar two or three times with about half its volume of 10% sulfuric acid. After the acid addition, the acid/tar mixture is stirred for about an hour at about 50 to 60° C. After settling, the bottom layer containing remaining acid and soluble salts is separated from the upper tar layer. By this method as much as 80% the salts can be removed with ash remaining in the tar at about 15–70 mg/kg (0.0015–0.007) by weight.

Another method also used 10% $H_2SO_4$ but in this method at a level of only 10% of the volume of the tar.

Still another method desalts phenol tar by a batch process, multi-stage washing with from 2–20 weight percent of the total tar weight of a 3–30 weight percent water solution of sulfuric acid. The batch is stirred holding the pH at no more than 7 at a temperature of from about 50 to abut 150° C. The tar is separated from the wash solution after settling for two hours. Salt is crystallized from the water layer at 20° C. The water layer after salt removal is reused to wash the next batch of tar. The tar after separation has a 0.15% by weight ash content and a 1.8% by weight water content. The pH of the extracted water is 5.2 and of the salt solution is from about 4 to 7.

These prior art methods have a number of disadvantages:

1) Substantial quantities of sulfuric acid are consumed resulting in additional material costs.

2) Use of sulfuric acid leads to high corrosion of process equipment and requires use of corrosion resistant alloys or linings.

3) Multi-stage washings result in generation of significant quantities of hazardous waste requiring treatment to minimize environmental detriment.

4) Multi-stage washings result in water consumption of 2–3 times the volume of tar processed.

5) Residual acid remains in tar leading to corrosion problems in subsequent tar processing steps and waste disposal after valuable components have been recovered.

6) When salt crystallization is employed, concentrated acidic salt wastes require neutralization before disposal.

It has now been found that these problems can be minimized if not completely avoided by the process of the present invention which comprises mixing with the tar a dilute aqueous orthophosphoric acid solution as the extraction agent, agitating the mixture, allowing the mixture to separate into two phases, an organic phase and an aqueous phase, and removing the aqueous phase from the organic phase. By employing this process at least 90% by weight of the salts are removed from the tar. In a preferred embodiment, at least 94% by weight of the salts are removed and in a more preferred embodiment at least 96% by weight of the salts are removed.

The present process can be conducted in either a batch mode or a continuous mode. When conducted in a batch mode, the tar and dilute aqueous solution of orthophosphoric acid are most conveniently mixed by stirring although any means of agitation may be used. To assure intimate mixing of the two phases, it is preferred that mixing continues for at least 10 min., more preferably at least 30 min. and still more preferably at least 60 min. The desalting process becomes economically inefficient if the mixing in a batch process continues for more than two hours. In a continuous mode, the mixing is most conveniently conducted by a flow of the dilute aqueous orthophosphoric acid solution countercurrent to the tar flow. This is preferably conducted in a vertical column with the aqueous phase entering the bottom of the column and the tar to be desalted entering the top of the column with desalted tar removed from the bottom portion in the column and the salt containing aqueous phase removed from the top portion of the column. The column may have baffles, trays or packing in order to enhance mixing of the phases. A key to successful operation of the process of the present invention is to provide sufficient contact between the salt containing tar and the aqueous phase after the phosphoric acid addition to assure that at least a substantial portion of the salts present and formed are transferred from the salt-containing tar to the aqueous phase.

Separation of the two phases occurs rapidly after cessation of agitation. Settling will preferably occur within two hours, more preferably within 1.5 hours and still more preferably within 0.5 hour.

While the process is useful for desalting tar containing any level of salts, it has been found preferable to desalt tar containing up to about 8% by weight of salts, more preferable up to about 5% by weight of salts and still more preferable up to about 3% by weight of salts. The process is also effective in removing salts from tar containing as little as 0.01% by weight of salts. However, it is usually economically more efficient to use this process if the tar contains at least 0.1% by weight of salts.

Although the amount of orthophosphoric acid in the dilute aqueous solution will depend on the tar pH, phase ratios, salt content of tar to be desalted, equipment in which the process operates and the mode of operation, it is preferred that the orthophosphoric acid content of the solution be in the range of from about 0.01% to about 3% by weight, more preferably from about 0.02% to about 2% by weight and still more preferably from about 0.03% to about 1% by weight. The pH of the tar may range from as low as 6 as high as 14, if it contains free caustic. The pH of the tar is more typically from about 7 to about 10.

The temperature at which the desalting takes place is not critical so long as the tar is flowable. Of course at elevated temperatures the viscosity of the tar decreases so that mixing of the two phases is more intimate and the desalting occurs more rapidly. Thus, it is preferred that the process be conducted at a temperature so that the temperature of the tar is at least 15° C., more preferably 50° C. and still more preferably 90° C. Since the desalting takes place between two liquids, the process is conducted below the boiling point of the aqueous solution or tar, whichever is lower. The process may be conducted at, above or below atmospheric pressure The advantages of the process are the following:

1. The use of weak acidic water solution of orthophosphoric acid allows the desalting of phenol tar of any composition without emulsion formation, which leads to significant shortening of phase settling time (not above 2 hours), depending on desalting mode.

2. The use of a less aggressive extraction agent compared with sulfuric acid significantly increases life of equipment.

3. Desalting is fulfilled in one stage, processing by extracting agent without further water washing, which significantly reduces water consumption as traces of acid in the processed tar do not raise problems of stack fume purification during tar incineration.

4. The use of weakly acidic water solution of orthophosphoric acid as extracting agent practically does not cause difficulties in further waste water utilization or biopurification stations as phosphates in small amounts are nutritive media for developing biological systems used.

5. The employment of a continuous countercurrent process of desalting allows reduction of both extracting agent concentration and its quantity.

The commercial uses of the process suggested are confirmed by the following examples which are provided to illustrate the invention and are not intended to limit in any way the scope thereof.

EXAMPLE 1

A phenol tar stream having a salt content of 0.846 wt. % with a pH for the water extract of 8.6 and a viscosity of 2240 cp @ 20° C. was stirred in a batch mixer with 0.30 wt. % orthophosphoric acid water solution with a phase mass ratio tar/extracting agent of 1/1.5, temperature of mixing was 90° C., time of processing 30 min., settling time 1.5 hours. Remaining salt content after settling was 0.008 wt. %, water content 4.8 wt. %.

EXAMPLE 2

A phenol tar stream having 0.116 wt. % of salts, a water extract pH of 8.7 and a viscosity of 59 cp. was stirred at 20° C. in a batch mixer with 0.25 wt. % phosphoric acid water solution. Mixing time was 30 min., settling time was 30 min. Remaining salt content was 0.003 wt. %. Degree of salt removal was 97.4%, water content in tar was 4.2 wt. %.

EXAMPLE 3

A phenol tar stream having 2.4 wt. % of salt, a viscosity of 2240 cp @ 20° C., and a water extract pH of 10.85 was processed in a countercurrent extractor by 0.05% phosphoric acid water solution with a phase mass ratio of 1:0.5 at 90° C. The remaining salt content in refinate was 0.07 wt. %, degree of salt removal was 97% and water content in the processed tar was 2.5 wt. %.

We claim:

1. A process to remove salts from a byproduct tar produced from the production of phenol from cumene, which process comprises:
    a) producing phenol and a byproduct tar from cumene,
    b) mixing the tar with dilute aqueous ortho phosphoric acid,
    c) agitating the mixture of tar and acid,
    d) separating the mixture into an aqueous phase and an organic phase, and
    e) removing the aqueous phase and whereby at least 90% by weight of salts are removed from the tar.

2. The process of claim 1 wherein the process is a batch process.

3. The process of claim 2 wherein the mixture is agitated for at least ten minutes.

4. The process of claim 3 wherein the mixture is separated by settling.

5. The process of claim 4 wherein the settling occurs within two hours.

6. The process of claim 1 wherein the process is a continuous process.

7. The process of claim 6 wherein the process is conducted in a vertical column.

8. The process of claim 7 wherein the dilute aqueous orthophosphoric acid enters the bottom of the column, the tar containing salts enters the top of the column, the organic phase leaves the bottom portion of the column and the aqueous phase leaves the top portion of the column.

9. The process of claim 1 wherein the tar contains up to about 8% by weight of salts.

10. The process of claim 1 wherein the tar contains at least 0.01% by weight of salts.

11. The process of claim 1 wherein the orthophosphoric acid content of the dilute aqueous orthophosphoric acid is from about 0.01% to about 3% by weight.

12. The process of claim 1 wherein the temperature of the tar is at least 10 C.

13. The process of claim 1 wherein the pH of the tar containing salts is at least 6.

* * * * *